United States Patent
Modglin

(10) Patent No.: US 9,943,433 B2
(45) Date of Patent: *Apr. 17, 2018

(54) CERVICAL COLLAR WITH CABLE ADJUSTMENT SYSTEM

(71) Applicant: DeRoyal Industries, Inc., Powell, TN (US)

(72) Inventor: Michael D. Modglin, Braselton, GA (US)

(73) Assignee: DeRoyal Industries, Inc., Powell, TN (US)

( * ) Notice: Subject to any disclaimer, the term of this patent is extended or adjusted under 35 U.S.C. 154(b) by 720 days.

This patent is subject to a terminal disclaimer.

(21) Appl. No.: 14/273,187

(22) Filed: May 8, 2014

(65) Prior Publication Data

US 2014/0243720 A1 Aug. 28, 2014

Related U.S. Application Data

(60) Continuation of application No. 13/780,165, filed on Feb. 28, 2013, now Pat. No. 8,721,576, which is a (Continued)

(51) Int. Cl.
*A61F 5/00* (2006.01)
*A61F 5/055* (2006.01)
*A61F 5/01* (2006.01)

(52) U.S. Cl.
CPC .............. *A61F 5/055* (2013.01); *A61F 5/01* (2013.01)

(58) Field of Classification Search
CPC ........ A61F 5/055; A61F 5/05883; A61F 5/01; Y10S 128/23; A61G 1/04; A61G 1/044; (Continued)

(56) References Cited

U.S. PATENT DOCUMENTS

| 4,968 A | 2/1847 | Knapp |
|---|---|---|
| 197,243 A | 11/1877 | Boylston |

(Continued)

FOREIGN PATENT DOCUMENTS

| ES | 2237303 A1 | 8/2003 |
|---|---|---|
| FR | 2704424 | 4/1993 |

(Continued)

OTHER PUBLICATIONS

J.H. Willard from Brownhelm, Ohio, U.S.A. Fracture Apparatus, Patented Jun. 11, 1836, U.S. Pat. No. Unknown 9720X.

(Continued)

*Primary Examiner* — Kim M Lewis
(74) *Attorney, Agent, or Firm* — Luedeka Neely Group, PC

(57) ABSTRACT

A cervical collar having a vertically adjustable chin support, the collar including a chin support adjustably connected to a collar body, the collar body defining an elongate slot; a cable located on the collar body; a cable stop connected to a distal portion of the cable and connecting between the collar body and the chin support, the cable stop being slidingly positionable along the slot on the collar body; and a pulley located on the collar body adjacent to the elongate slot. The cable cooperates with the pulley so that the direction of the cable is changed between the cable stop and a proximal portion of the cable, and movement of the distal portion of the cable adjusts the position of the cable stop along the slot and adjusts the vertical position of the chin support relative to the collar body.

3 Claims, 15 Drawing Sheets

Related U.S. Application Data division of application No. 13/226,151, filed on Sep. 6, 2011, now Pat. No. 8,449,485.

(58) Field of Classification Search
CPC ........... A61G 7/072; A43C 1/00; A43C 11/00; A43C 11/16; A43C 11/20
USPC .............. 602/17–19; 128/DIG. 23, 845
See application file for complete search history.

(56) References Cited

U.S. PATENT DOCUMENTS

| | | | |
|---|---|---|---|
| 1,930,440 A | 10/1933 | Longfellow | |
| 2,474,200 A | 6/1949 | McBee | |
| 2,791,999 A | 5/1957 | Bustamante | |
| 3,042,027 A | 7/1962 | Monfardini | |
| 3,521,057 A | 7/1970 | Morlan | |
| 3,596,655 A | 8/1971 | Corcoran | |
| 4,888,831 A | 12/1989 | Oleson | |
| 5,005,563 A | 4/1991 | Veale | |
| 5,302,170 A | 4/1994 | Tweardy | |
| 5,688,229 A | 11/1997 | Bauer | |
| 5,865,773 A | 2/1999 | Koledin | |
| 5,993,403 A | 11/1999 | Martin | |
| 6,315,746 B1 | 11/2001 | Garth et al. | |
| 6,423,020 B1 | 7/2002 | Koledin | |
| 6,503,213 B2 | 1/2003 | Bonutti | |
| 6,599,257 B2 | 7/2003 | Al-Obaidi et al. | |
| 6,770,047 B2 | 8/2004 | Bonutti | |
| 7,090,652 B2 * | 8/2006 | Santelli, Jr. | A61F 5/055 128/DIG. 23 |
| 7,120,954 B2 | 10/2006 | Traut et al. | |
| 7,128,724 B2 | 10/2006 | Marsh | |
| 7,297,127 B2 | 11/2007 | Lee et al. | |
| 7,371,222 B2 | 5/2008 | Heinz et al. | |
| 7,674,234 B2 | 3/2010 | Calco et al. | |
| 7,806,842 B2 * | 10/2010 | Stevenson | A61F 5/0125 602/16 |
| 7,954,204 B2 | 6/2011 | Hammerslag et al. | |
| 7,992,261 B2 | 8/2011 | Hammerslag et al. | |
| 8,251,934 B2 | 8/2012 | Bonutti | |
| 8,303,527 B2 * | 11/2012 | Joseph | A61F 5/01 128/869 |
| 2004/0204666 A1 | 10/2004 | Marsh | |
| 2005/0113728 A1 * | 5/2005 | Heinz | A61F 5/055 602/18 |
| 2006/0135897 A1 | 6/2006 | Dellanno | |
| 2007/0027418 A1 * | 2/2007 | Calco | A61F 5/055 602/18 |
| 2008/0066272 A1 * | 3/2008 | Hammerslag | A43C 11/14 24/712 |
| 2008/0091132 A1 * | 4/2008 | Bonutti | A61F 5/055 602/32 |
| 2008/0249448 A1 | 10/2008 | Stevenson et al. | |
| 2009/0149788 A1 | 6/2009 | Dellanno | |
| 2009/0287128 A1 | 11/2009 | Ingimundarson et al. | |
| 2010/0268139 A1 | 10/2010 | Garth | |
| 2011/0167543 A1 * | 7/2011 | Kovacevich | F41H 1/04 2/417 |
| 2013/0060179 A1 | 3/2013 | Modglin | |
| 2013/0281899 A1 * | 10/2013 | Suarez | A61F 5/055 602/18 |
| 2013/0281900 A1 * | 10/2013 | Suarez | A61F 5/055 602/18 |
| 2016/0287424 A1 * | 10/2016 | Webster | A61F 5/055 |

FOREIGN PATENT DOCUMENTS

| | | |
|---|---|---|
| GB | 862277 | 3/1961 |
| GB | 1132607 | 11/1968 |
| GB | 1290523 | 9/1972 |
| GB | 2194156 A | 3/1988 |
| GB | 2233900 A | 1/1991 |
| JP | 0326251 | 2/1991 |
| JP | 0721013 | 7/1995 |
| WO | 2005117769 A1 | 12/2005 |
| WO | 2008033963 A2 | 3/2008 |
| WO | 2008033963 A3 | 3/2008 |
| WO | 2010117749 A2 | 10/2010 |
| WO | 2010117749 A3 | 10/2010 |

OTHER PUBLICATIONS

Frontier Medical New Zealand Ltd, 4 Fisher Crescent, Mt. Wellington, Auckland, New Zealand Ferno Wizloc Cervial Collar-Military Spec FW-WLG Copyright 2008 www.frontmed.co.nz.
Dellanno of Bloomfield, New Jersey, U.S.A. Forward Head Posture Correction Collar U.S. Appl. No. 60/638,061, filed Dec. 21, 2001.
Japanese Patent No. JPH0284614U No translation available, Jul. 1990.
European Patent Office Search Report dated Jan. 29, 2015 Application EP 12 83 9427 (6 pages).
European Patent Office, Extended European Search Report, Application 14196751.3-1654 dated Mar. 18, 2015.

* cited by examiner

CERVICAL COLLAR WITH CABLE ADJUSTMENT SYSTEM

CROSS-REFERENCE TO RELATED APPLICATION

This application is a continuation of co-pending (Allowed) U.S. application Ser. No. 13/780,165, filed Feb. 28, 2013, and entitled Cervical Collar With Cable Reel Adjustment System, which is a divisional application of U.S. application Ser. No. 13/226,151, filed Sep. 6, 2011, and entitled Cervical Collar With Cable Reel Adjustment System (now U.S. Pat. No. 8,449,485), each incorporated by reference herein in its entirety.

FIELD

This disclosure relates to the field of size adjustable cervical collars. More particularly, the disclosure relates to cervical collars that enable improved adjustment of the height of the chin support.

BACKGROUND

Cervical collars are used to maintain the spine of a patient in a desired orientation by immobilizing the neck of the patient and supporting the chin at a desired, generally level or neutral position. The position of the chin is maintained by locating a chin support to contact and support the underside of the chin at a desired angle.

The expense of cervical collars has resulted in various forms of adjustable collars that enable a single collar model to be used for a variety of patient sizes. However, a desire for improvement in the construction of adjustable collars remains.

SUMMARY

The disclosure relates to a cervical collar having a vertically adjustable chin support. In one aspect, the collar includes a chin support adjustably connected to a collar body configured to be positioned adjacent a neck of a patient, the collar body defining an elongate slot; a cable connected to a rotatable cable reel located on the collar body; a cable stop connected to the cable and connecting between the collar body and the chin support, the cable stop being slidingly positionable along the slot on the collar body; and a pulley located on the collar body adjacent to the elongate slot. The cable cooperates with the pulley so that the direction of the cable is changed between the cable stop and the cable reel, and rotation of the cable reel adjusts the cable to adjust the position of the cable stop along the slot and adjusts the vertical position of the chin support relative to the collar body.

In another aspect, a cervical collar having a vertically adjustable chin support includes a chin support adjustably connected to a collar body, the collar body defining an elongate slot; a cable located on the collar body; a cable stop connected to a distal portion of the cable and connecting between the collar body and the chin support, the cable stop being slidingly positionable along the slot on the collar body; and a pulley located on the collar body adjacent to the elongate slot. The cable cooperates with the pulley so that the direction of the cable is changed between the cable stop and a proximal portion of the cable, and movement of the distal portion of the cable adjusts the position of the cable stop along the slot and adjusts the vertical position of the chin support relative to the collar body.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1A:
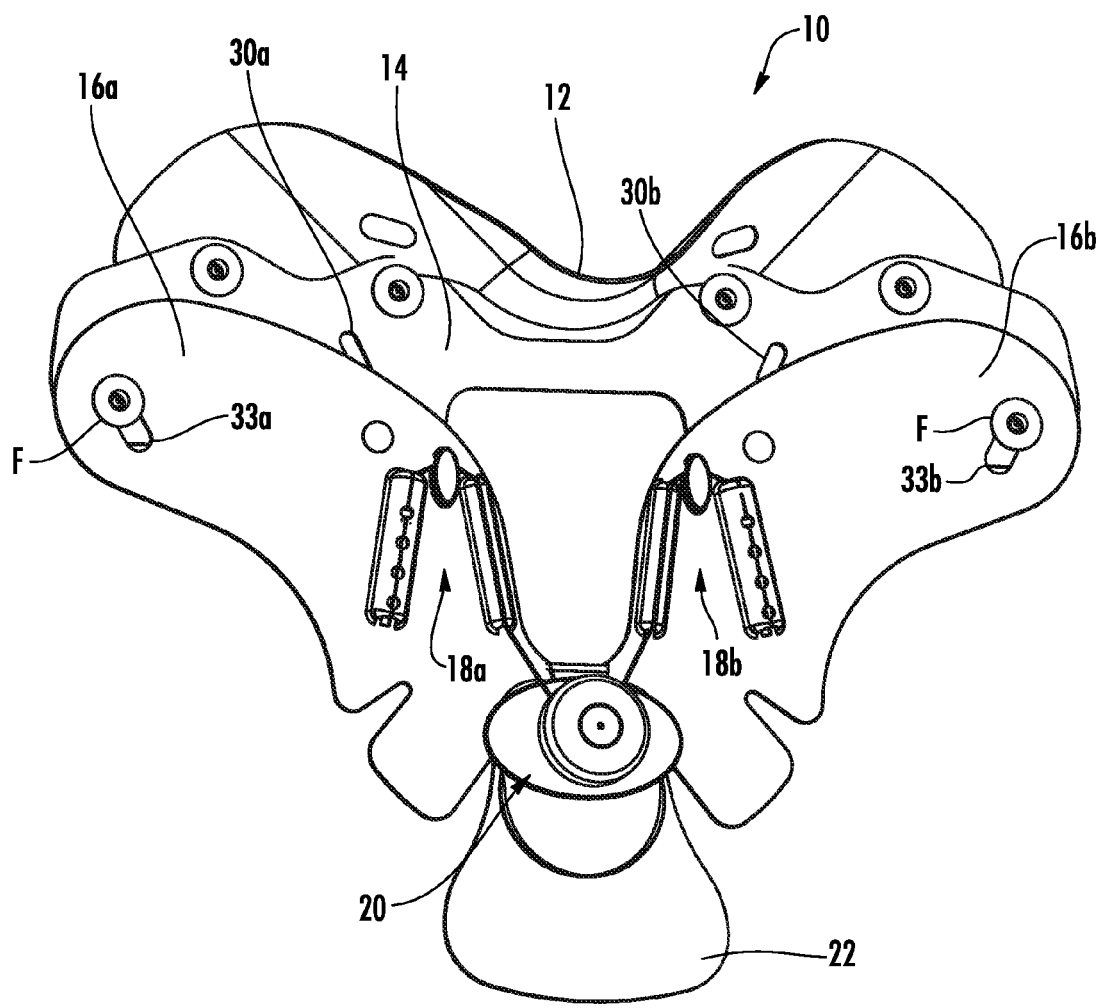
FIG. 1A is a front plan view of a front assembly for a cervical collar according to the disclosure adjusted to locate a chin support thereof to a first position.

With reference to the drawings, the disclosure relates to an adjustable body support. The body support may be configured to adjustably support the chin of a user, or other anatomical portions of a patient.

In a preferred embodiment, the body support is a cervical collar 10 configured to enable adjustment of the height of a chin support 12 of the collar 10. The collar 10 also includes an adjustable front assembly having a front main body 14, front adjustable body portions 16a and 16b, cable tensioning systems 18a and 18b, and a cable reel 20. The front assembly may also include a sternal pad 22. The collar 10 also includes a rear assembly 24 having an occipital support 26 and a posterior support 28.

The cervical collar 10 is positioned about the neck of a user with the front assembly 14 situated at the front of the user with the chin of the user resting in the chin support 12, and the rear assembly 24 at the back of the user. The front assembly 14 and the rear assembly 24 are adjustably secured together as by straps to comfortably but snugly fit the neck of the user to restrain movement of the neck. The front assembly 14 is adjusted to situate the chin support 12 to maintain the chin of the user at a desired orientation, typically level.

The chin support 12 is of one-piece molded plastic construction, such as low density polyethylene) and is characterized as having a central located u-shaped portion 12a, with adjacent side wings 12b and 12c on either side of the u-shaped portion 12a. The u-shaped portion 12a is suitably shaped to receive the chin of a user for supporting the chin and may include padding or the like for additional comfort of the user if desired. The chin support 12 is mounted to front main body 14 as by plastic rivets.

The front main body 14 is of one-piece molded plastic construction and is characterized as having a central connector 14a bridging between adjacent side wings 14b and 14c. The connector 14a spans between upper portions of the side wings 14b and 14c, to define a cut-out for providing clearance for a tracheal tube of the like. The wings 14b and 14c include elongate, and preferably curved, slots 30a and 30b, respectively. The slots 30a and 30b receive fasteners F or the like inserted through aligned apertures 31a and 31b, respectively, of the adjustable body portions 16a and 16b. The fasteners F are preferably plastic, but may be other materials suitable for use in a cervical collar. The chin support 12 and the main body 14 may be provided as a unitary piece; however, having them as separate portions enables better conformity to the anatomy of the patient. Also, the adjustable body portions 16a and 16b may be provided as a single body portion, but, are preferably provided as two pieces that pivotally connect as described herein for improved conformity to the patient throughout the range of the height adjustment of the chin support 12.

The adjustable body portion 16a is of one-piece molded plastic construction and is configured to overlie about one-half of the sterna or upper chest region of the patient. The adjustable body portion 16b is substantially a mirror image of the body portion 16b for overlying the other about one-half of the sterna or upper chest region of the patient. The body portions 16a and 16b overlap at their lowermost portions and pivotally attach to one another as by a rivet, fastener, or the like extending through aligned apertures 37a and 37b thereof. The body portion 16a includes a slot 33a adjacent a distal or raised end thereof, and the body portion 16b includes a slot 33b adjacent a distal or raised end thereof. The sternal pad 22 includes an aperture 22a that is aligned with the apertures 37a and 37b, so that the fastener used to pivotally attach the body portions 16a and 16b also attaches the sterna pad 22. The slots 33a and 33b align with apertures 35a and 35b located on the side wings 14b and 14c of the main body 14, respectively, and receive fasteners or the like, such as the fasteners F.

The cable tensioning system 18a is located on the exterior of the body portion 16a and includes a cable guide 32, a pulley 34, a spring 36 located within a spring housing 38, and a cable stop 40. The pulley 34 may be a roller pulley or a simple knob or projection for changing the direction of the cable trained over it. Thus, the term "pulley" will be understood to mean a structure that changes the direction of a cable trained over it.

Figure 4:
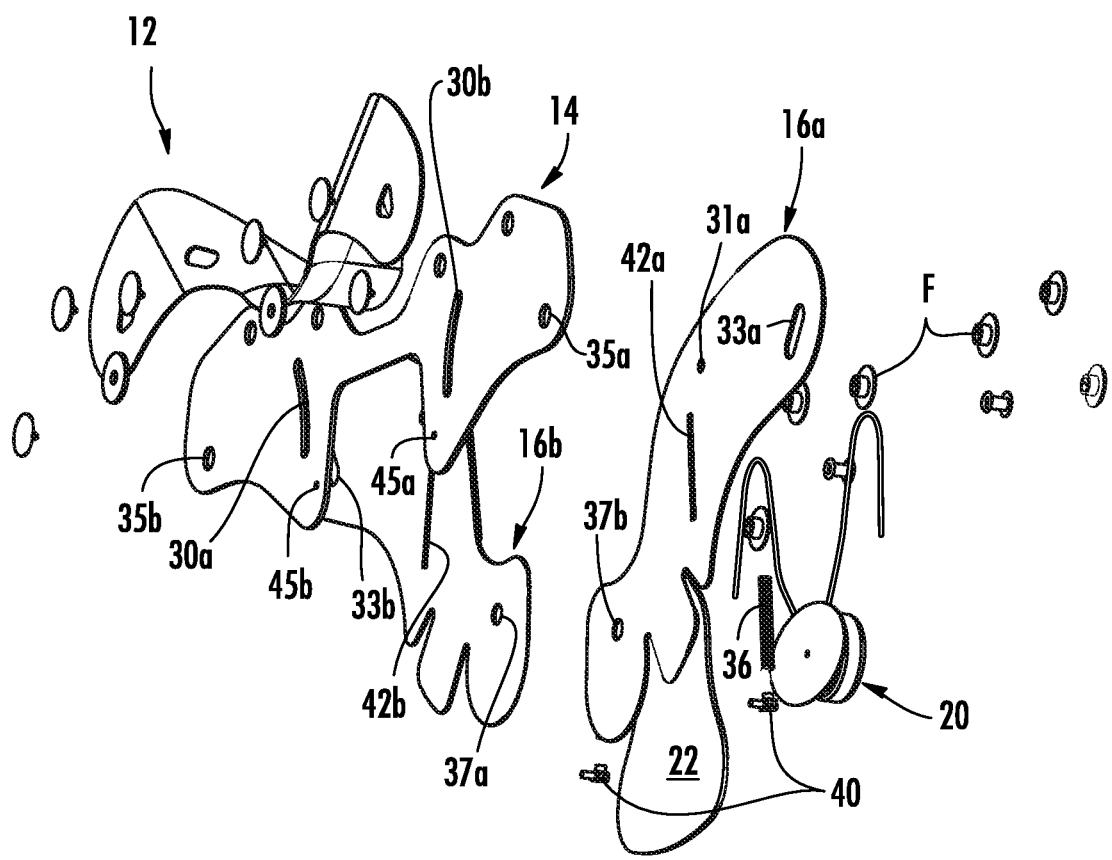
FIG. 4 is a rear exploded perspective view thereof.
Figure 5:
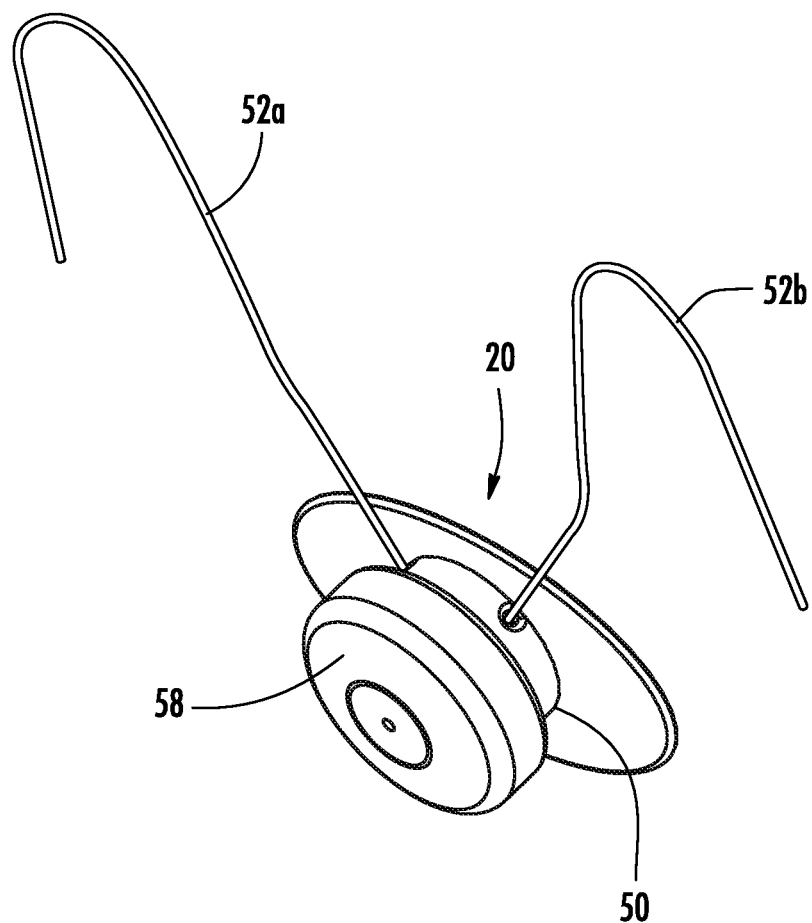
FIG. 5 is a perspective view of a cable reel component of the front assembly of FIGS. 3 and 4.
Figure 6:
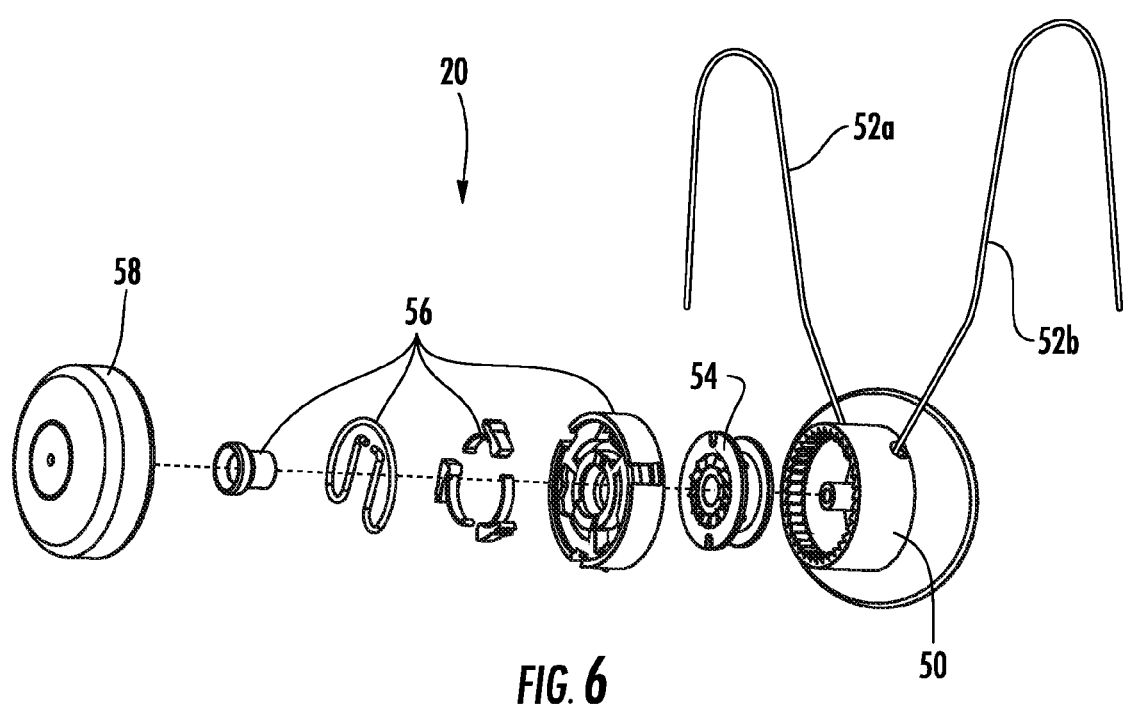
FIG. 6 is an exploded view thereof.
Figure 7:
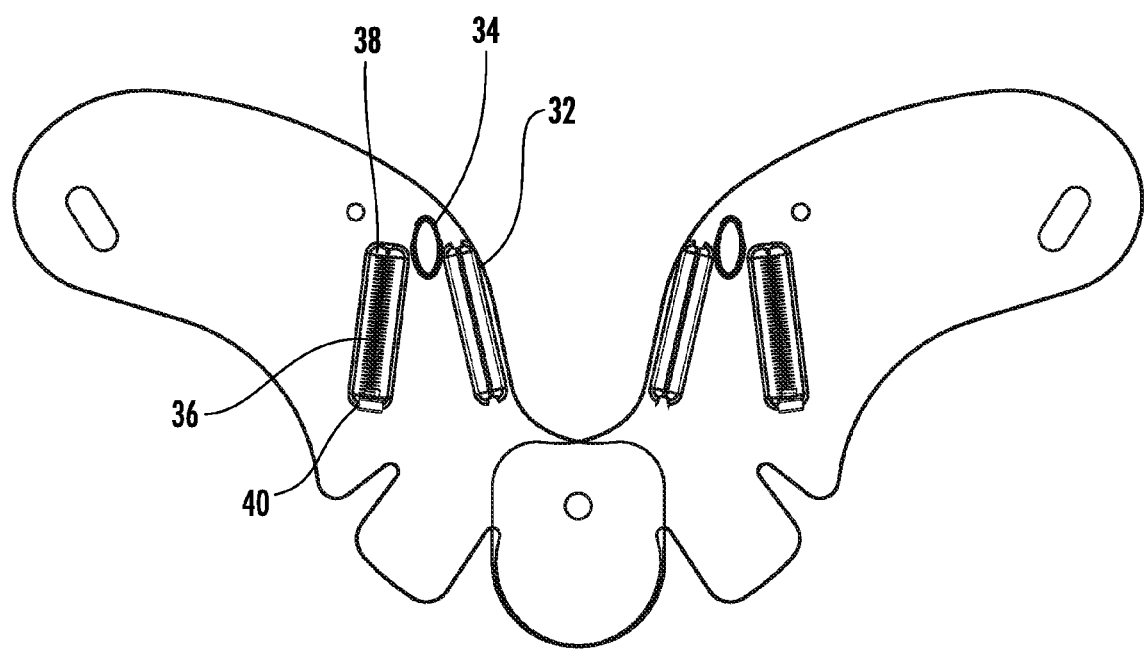
FIG. 7 is a detailed front view showing components for maintaining cable tension.
Figure 8:
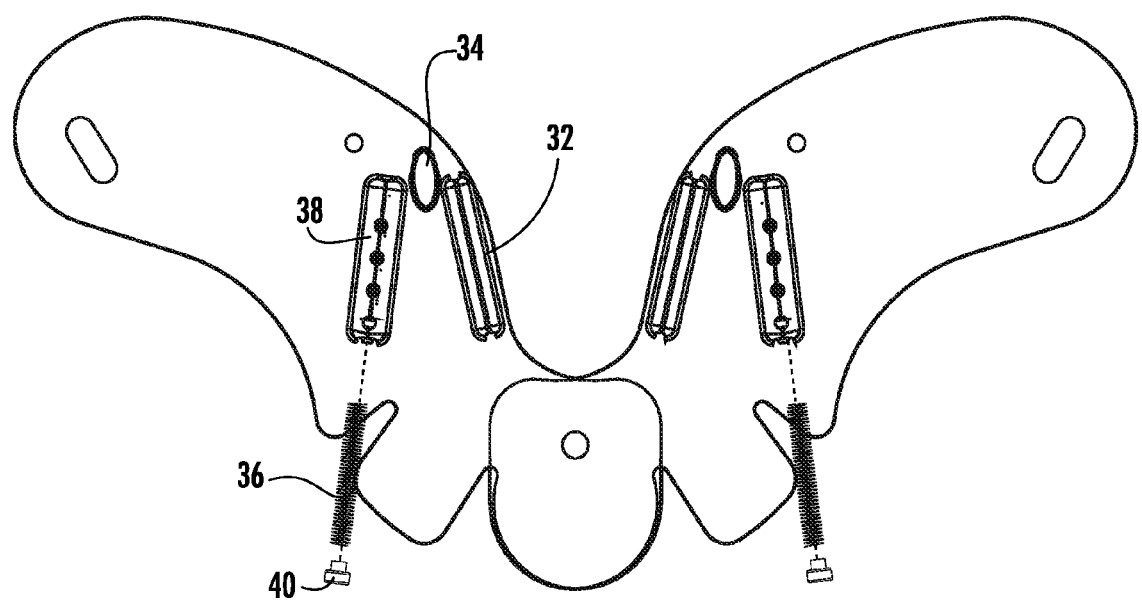
FIG. 8 is an exploded view thereof.

The spring 36 is a compression spring that gets shorter as a load is applied to it, as explained more fully below. The spring housing 38 is an enclosure for enclosing the spring so that as a load is applied to the distal or lower end of the spring, the proximal or upper end of the spring bears against spring housing 38. The spring housing 38 overlies a slot 42a defined on the adjustable body portion 16a (FIG. 4) and located to align with a corresponding aperture of the body portion 14. The cable stop 40 is a plastic knob or the like that is located adjacent to and in engagement with the distal end of the spring 36 within the spring housing 38.

Figure 10:
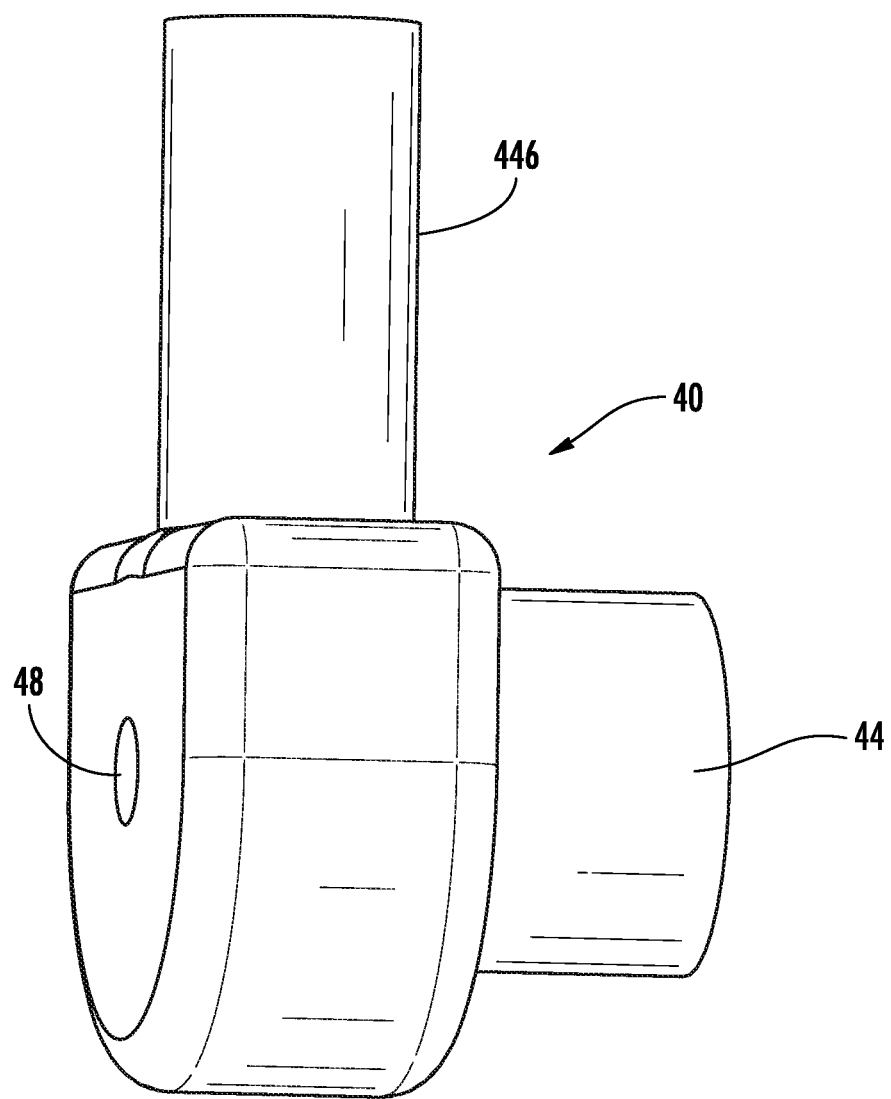
FIG. 10 shows a cable stop component of the cervical collar according to the disclosure.
Figure 11:
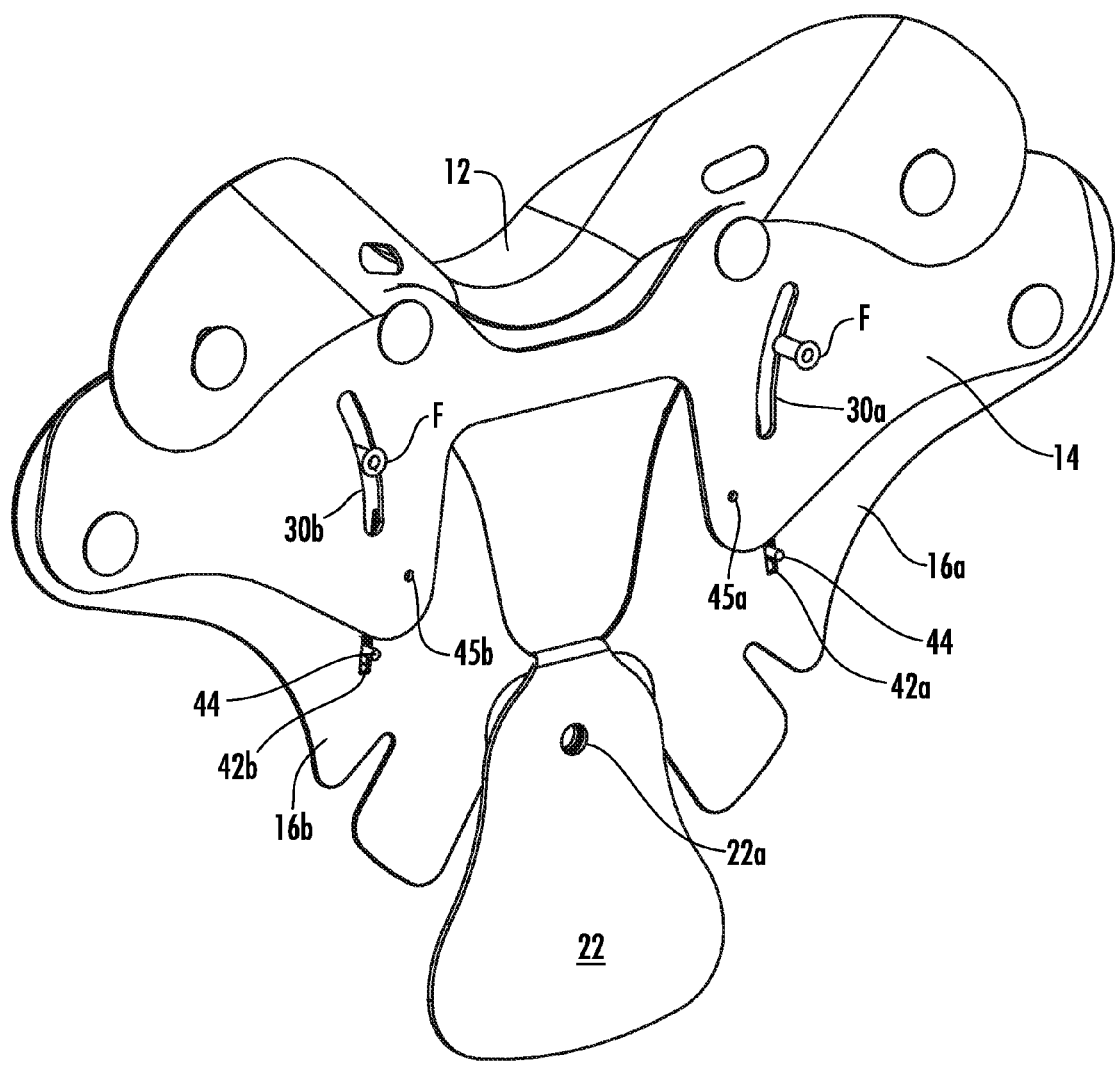
FIG. 11 is a rear assembled view of the front assembly of FIG. 1A.

The cable stop 40 includes a projection 44 (FIG. 10) that extends through the slot 42a and a corresponding aperture 45a of the body portion 14 and is captured by a plastic washer or the like to connect the main body portion 14 and the adjustable body portion 16a, with the main body portion 14 being able to move relative to the adjustable body portion 16a commensurate with the slot 42a. A cylindrical shaft 46 perpendicular to the projection 44 may be provided for receiving the end of the spring 36. In this regard, the cable 52a may be passed through the spring 36, through the shaft 46, and out of an aperture 48 of the cable stop 40, and secured as by a fastener or knot or the like to secure the cable 52a to the cable stop 40.

The cable tensioning system 18b is substantially identical to the cable tensioning system 18a and is located on the exterior of the body portion 16b, with the spring housing 38 thereof overlying a slot 42b defined the adjustable body portion 16b, with the projection 44 of the cable stop 40 extending into an aperture 45b of the body portion 14.

The cable reel 20 is a rotating spool that winds or unwinds cable and, preferably includes a toothed housing 50 mounted onto the front body portion 16a. The housing 50 is configured for receiving a pair of cables 52a and 52b, each having a proximal end rotationally linked to a spool 54 contained within the housing 50. The opposite distal ends of the cables 52a and 52b are connected to the cable stop 40 of the cable tensioning systems 18a and 18b, respectively. A knob 56 having a spring-loaded assembly 58 cooperates with the housing 50 and the spool 54 for manually winding the cables 52a and 52b around the spool 54. The knob 54 includes a pawl integrally formed on an inner surface of the knob 54 to selectively engage the teeth of the housing 50 to provide a ratchet feature for winding the spool 54 when the knob 56 is turned in one direction to tension the cables 52a and 52b. The spring-loaded assembly 58 is depressed to release the teeth of the knob 54 from engagement with the housing 50 to allow the spool to be released to untension the cables 52a and 52b. Suitable devices to use for the cable reel 20 are cable reel devices available under the name BOA from Boa Technology, Inc. of Denver, Colo., and described in U.S. Pat. Nos. 7,954,204 and 7,992,261, incorporated by reference in their entireties.

Figure 9A:
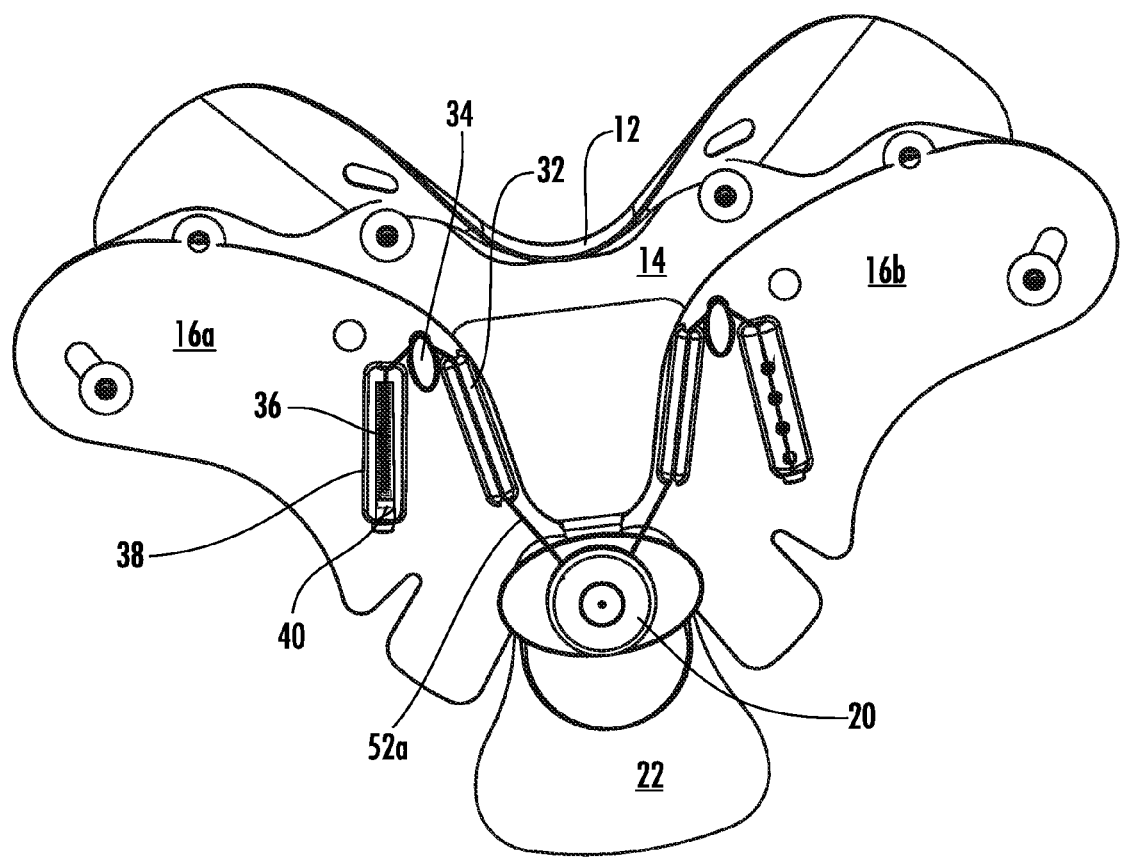
FIG. 9A shows positioning of the cable tension components when the chin support is at the low position of FIG. 1A.
Figure 9B:
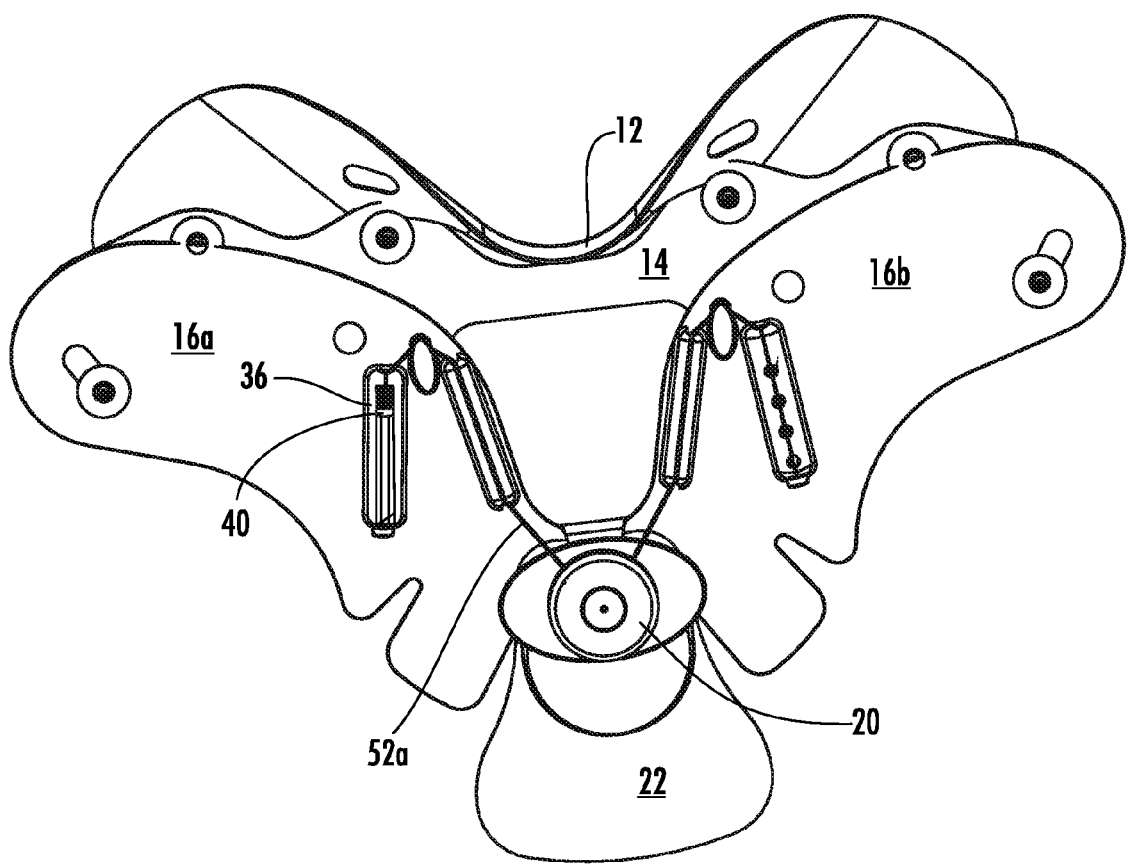
FIG. 9B shows positioning of the cable tension components when the chin support is at the high position of FIG. 1B.

By utilizing the cable reel 20 to adjust the lengths of the cables 52a and 52b, the cable tensioning systems 18a and 18b are utilized to vertically adjust the position of the chin support 12 relative to the body portions 16a and 16b which remain substantially statically positioned around the neck of the user. In this regard, and with reference to FIG. 9A, it will be seen that the cable 52a is of a length as provided by manipulation of the reel 20, so that the cable stop 40 of the tensioning system 18a is at a lowermost position of the housing 38. This position of the cable stop 40 corresponds to the chin support 12 being at its lowermost vertical height. Next, with reference to FIG. 9B, it will be seen that the cable 52a has been retracted by use of the reel 20 to position the cable stop 40 at an uppermost position of the housing 38. This position of the cable stop 40 corresponds to the chin support 12 being at its uppermost vertical height. As will be appreciated, by adjusting the lengths of the cables 52a and 52b using the reel 20, the chin support 12 may be positioned at any vertical height within the range of the uppermost and lowermost positions of the cable stop 40. Also, as the reel 20 uniformly winds and unwinds the cables 52a and 52b, the tensioning systems 18a and 18b are substantially uniform in their adjustment so that the chin support remains substantially level. However, if it were desired to have an adjustment system that enabled canted or non-level adjustment, the same may be accomplished by adjusting the positions of the tensioning systems 18a and 18b relative to one another or otherwise enabling different cable length adjustments.

Provision of the compression spring 36 for the tensioning systems 18a and 18b is advantageous so as to maintain a downward bias on the cable stops 40 to minimize free play of the cable stops 40. In this regard, it will be observed that in FIG. 9B, the spring 36 is substantially extended and bearing against the stop 40, and in FIG. 9B the spring 36 is substantially compressed and bearing against the cable stop 40. It will be appreciated that other bias members may be used to maintain a downward bias on the cables tops 40. For example, a rubber band 60 or the like may be attached to the cable stop 40 and to a fixed point below the stop 40, such as anchor 62, to maintain a downward bias on the cable stop 40.

The adjustable front assembly is assembled so that the front adjustable body portions 16a and 16b overlap at their lowermost portions and attach to one another as by plastic rivets extending through aligned apertures thereof, with the cable reel 20 mounted to the body portion 16a. The adjustable body portions 16a and 16b do not move, but are adjusted by use of the cable tensioning systems 18a and 18b to adjust the vertical position of the front assembly 14 relative to the adjustable body portions 16a and 16b to desirably situate the chin support 12 mounted to the front assembly.

The front assembly 14 is movably mounted to the adjustable body portions 16a and 16b by the projections 44 of the cable stops 40 that extend through the slots 42a and 42b, respectively, and the corresponding apertures 45a and 45b of the body portion 14 and captured by plastic washers or the like to connect the main body portion 14 and the adjustable body portions 16a and 16b. Thus, by utilizing the cables 52a and 52b to move the cable stops 40 vertically within the slots 42a and 42b by operation of the cable reel 20, the main body portion 14 is vertically adjusted relative to the adjustable body portions 16a and 16b commensurate with the limits of the slots 42a and 42b.

In addition, as other portions of the main body portion 14 and the adjustable body portions 16a and 16b are attached to one another as by fasteners, the slots 30a and 30b of the adjustable body portions 16a and 16b accommodate additional relative positioning commensurate with the vertical adjustment resulting from adjustment of the positions of the cable stops 40 of the cable tensioning systems 18a and 18b using the cable reel 20. Also, the provision of the adjustable body portions 16a and 16b as separate pieces and the ability of the adjustable body portions 16a and 16b to pivot relative to one another enables improved conformity of the collar 10.

Figure 1B:
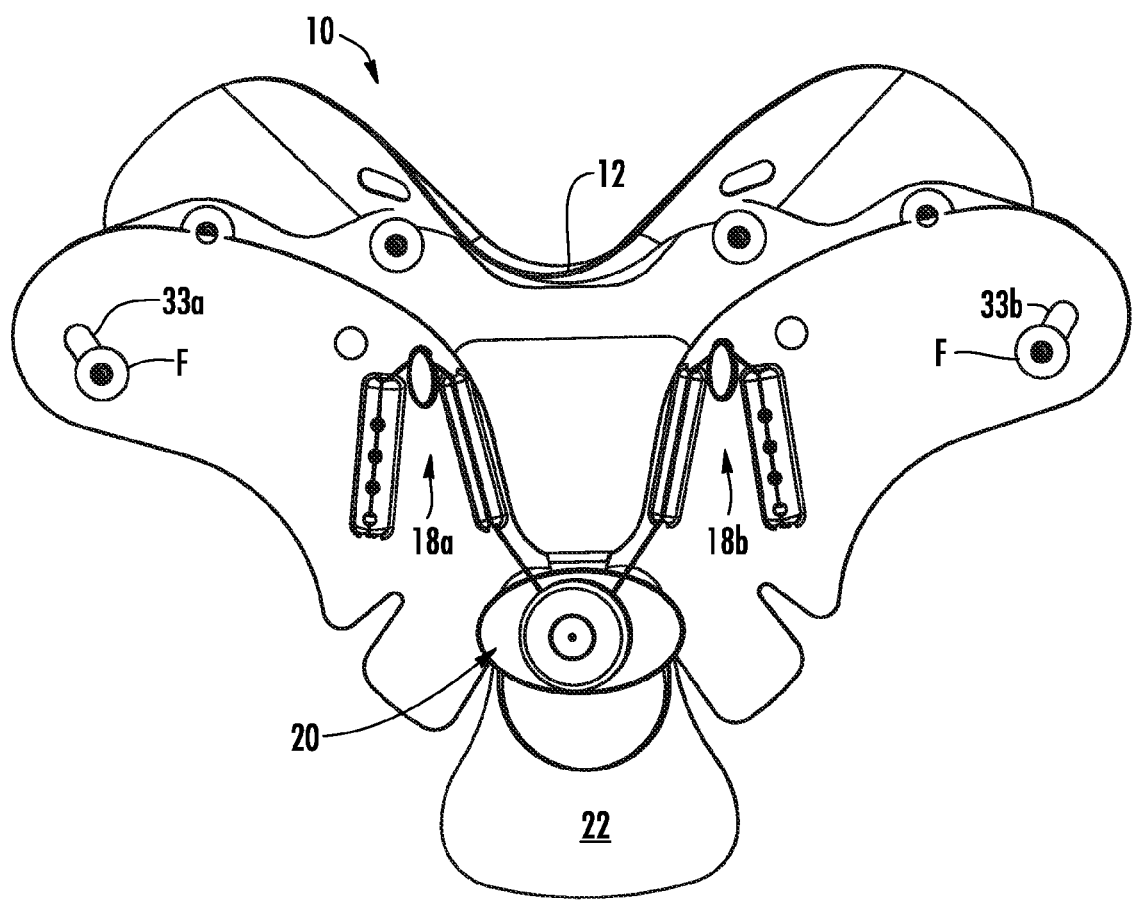
FIG. 1B shows the front assembly of FIG. 1A adjusted to locate the chin support to a second and higher position.
Figure 2:
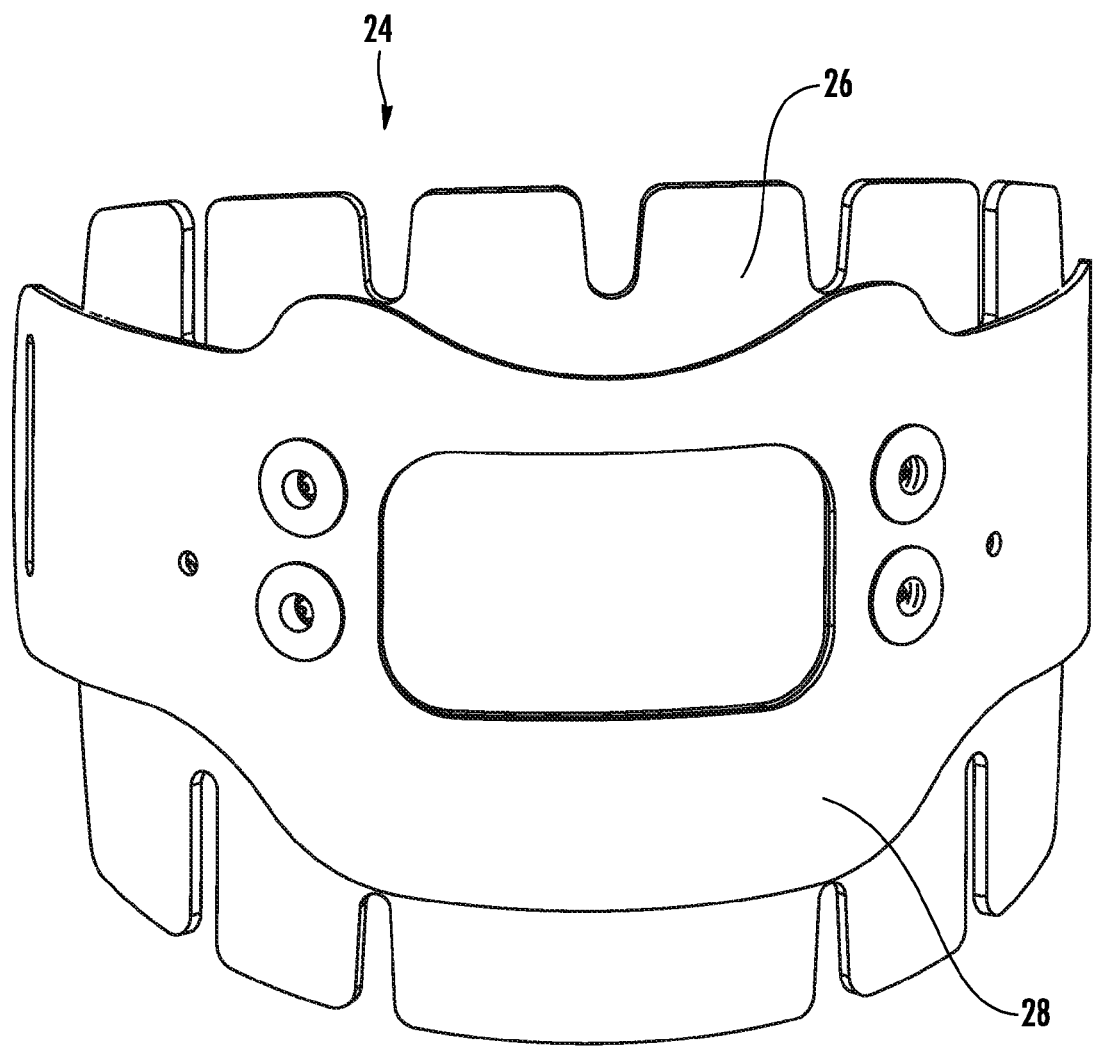
FIG. 2 shows a back assembly of a cervical collar according to the disclosure.
Figure 3:
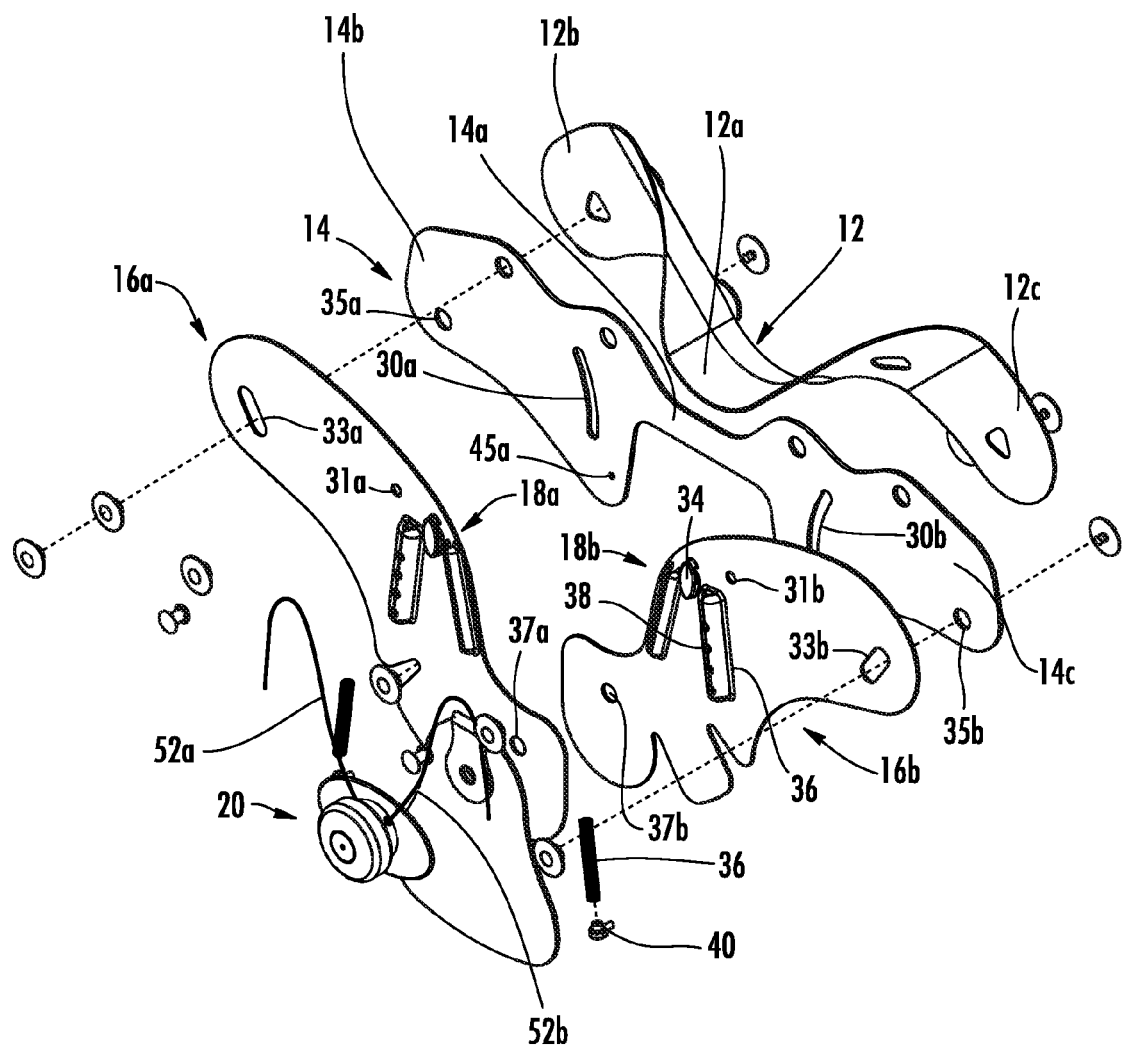
FIG. 3 shows a front exploded perspective view of the front assembly of FIG. 1A.

The chin support 12 is fixedly mounted to the main body portion 14 as by mutually aligned apertures and plastic fasteners. Thus, as the main body portion 14 is vertically adjusted using the tensioning systems 18a and 18b, the chin support 12 is likewise vertically adjusted relative to the relative to the positions of the body portions 16a and 16b. For example, with reference to FIGS. 1A and 1B, it will be seen that the chin support 12 is vertically higher in FIG. 1A than in FIG. 1B, it being understood that the adjustment of the position of the chin support 12 is accomplished by use of the cable tensioning systems 18a and 18b as previously described.

Figure 12A:
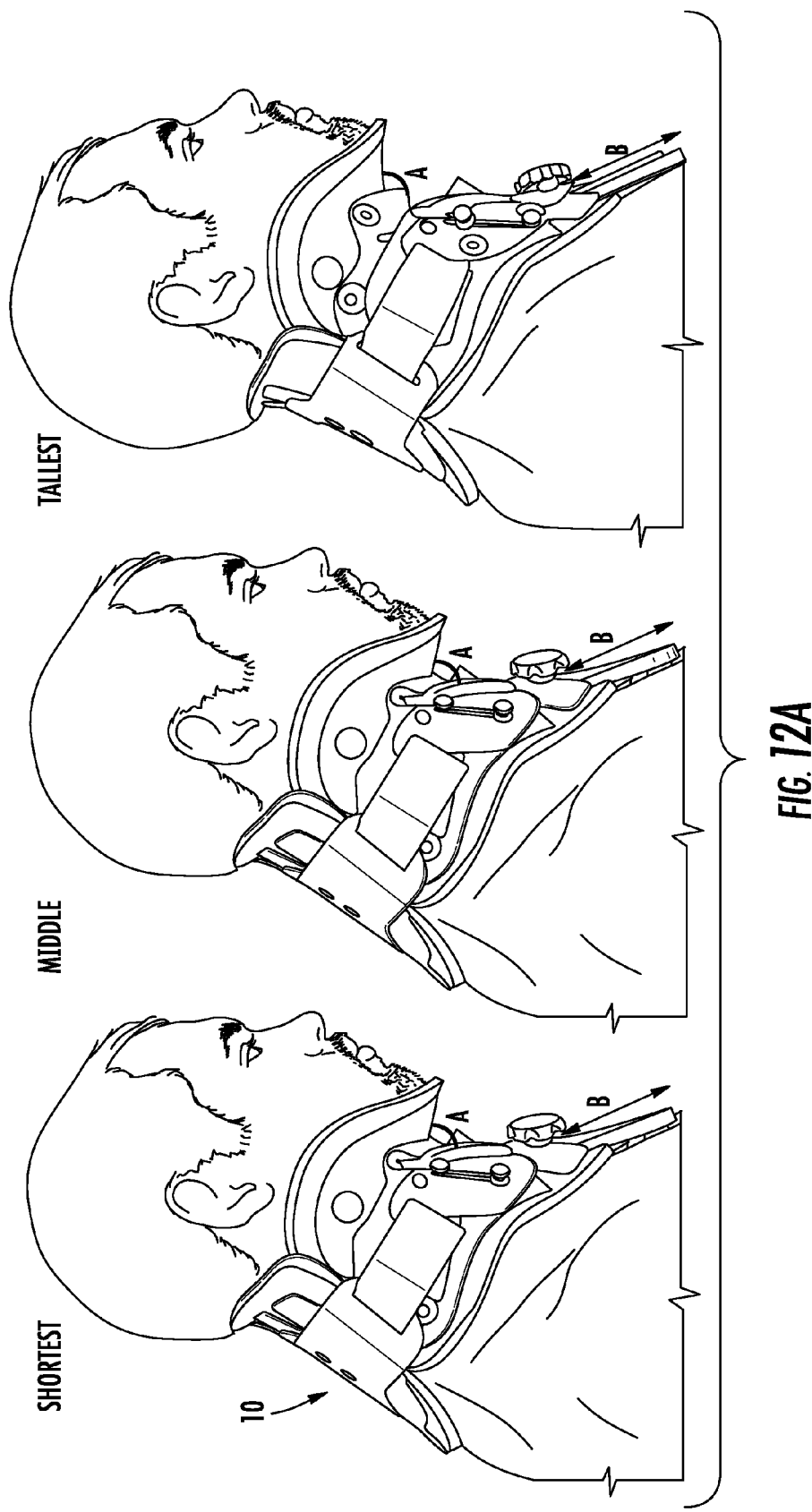
FIGS. 12A and 12B illustrate vertical adjustment of the chin support in a manner such that the orientation of the chin support remains substantially constant in all vertical positions of the chin support.
Figure 12B:
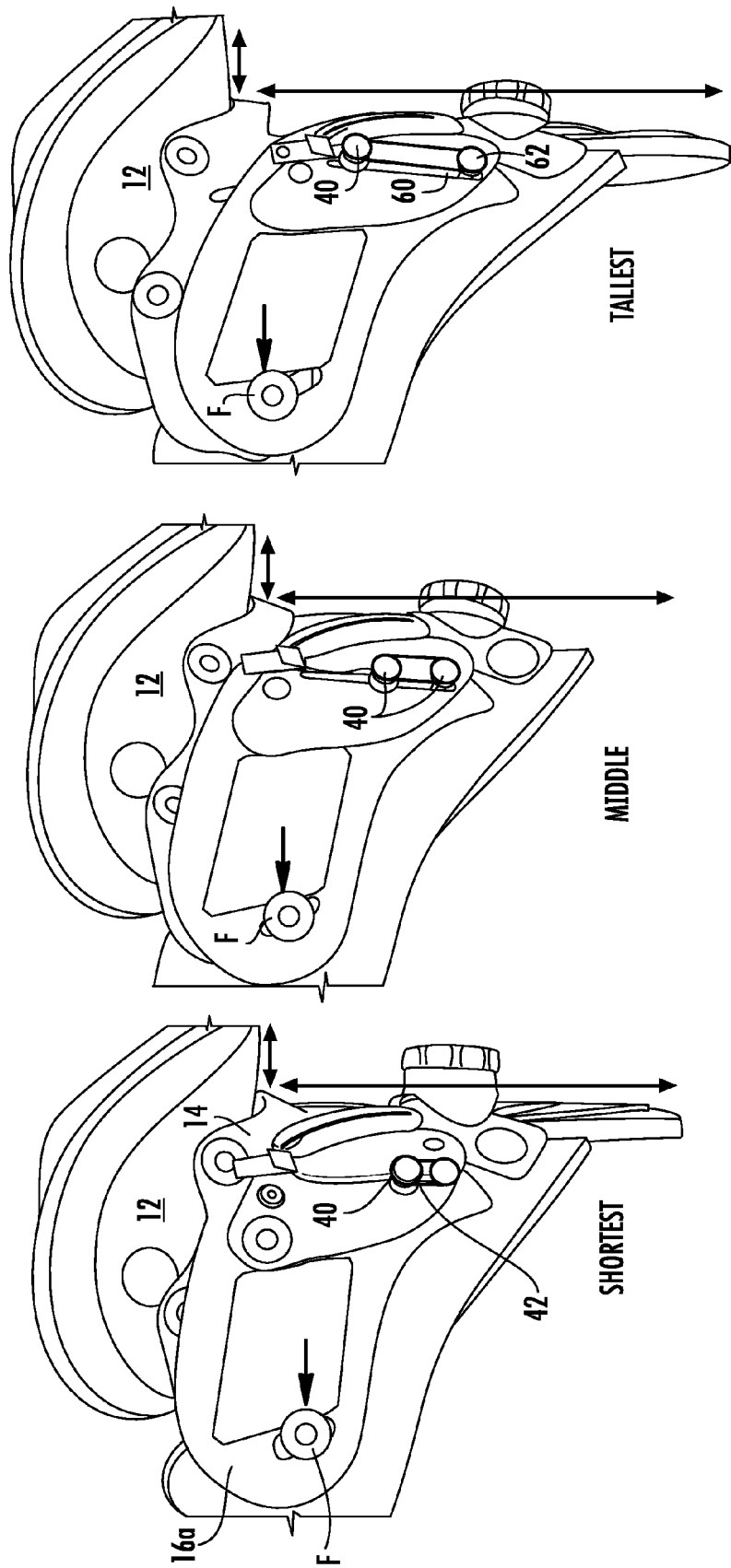

The structure of the collar 10 also advantageously enables vertical adjustment of the chin support 12 in a manner such that the orientation of the chin support 12 remains substantially constant in all vertical positions of the chin support 12. For example, with reference to FIGS. 12A and 12B, there is shown the collar 10 with the chin support 12 positioned (from right to left) in the lowest, middle, and highest positions. However, despite the vertical height of the chin support 12, an angle A between the chin support 12 and the adjustable body portions 16a and 16b remains substantially constant, preferably about 90 degrees. Also, the structure of the collar 10 also advantageously enables the sternal pad 22 to remain in substantial conformity with the anatomy of the patient despite adjustments of the vertical height of the chin support 12, as indicated by arrow B. The vertical adjustability of the chin support 12 in this manner is accomplished by the provision of the cable stops 40 in combination with the slots 42a and 42b. In addition, the slots 30a and 30b on the main body 14 and the slots 33a and 33b on the adjustable body portions 16a and 16b, enable the described adjustments, while maintaining conformity with the anatomy of the patient.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A cervical collar having a vertically adjustable chin support, the collar comprising:
    a chin support adjustably connected to a collar body configured to be positioned adjacent a neck of a patient, the collar body defining an elongate slot;
    a cable connected to a rotatable cable reel located on the collar body;
    a cable stop connected to the cable and connecting between the collar body and the chin support, the cable stop being slidingly positionable along the elongated slot on the collar body; and
    a pulley located on the collar body adjacent to the elongate slot, wherein the cable cooperates with the pulley so that a direction of the cable is changed between the cable stop and the cable reel, and rotation of the cable reel adjusts the cable to adjust the position of the cable stop along the elongated slot and adjusts a vertical position of the chin support relative to the collar body.

2. The collar of claim 1, further comprising a main collar body connected to the cable stop and connected to the chin support.

3. A cervical collar having an adjustable chin support, the collar comprising:
    a chin support adjustably connected to a collar body, the collar body defining an elongate slot;
    a cable located on the collar body;
    a cable stop connected to a distal portion of the cable and connecting between the collar body and the chin support, the cable stop being slidingly positionable along the elongated slot on the collar body; and
    a pulley located on the collar body adjacent to the elongate slot, wherein the cable cooperates with the pulley so that a direction of the cable is changed between the cable stop and a proximal portion of the cable, and movement of the distal portion of the cable adjusts the position of the cable stop along the elongated slot and adjusts a vertical position of the chin support relative to the collar body.

* * * * *